(12) United States Patent
Mendoza et al.

(10) Patent No.: US 10,699,480 B2
(45) Date of Patent: Jun. 30, 2020

(54) SYSTEM AND METHOD FOR PROVIDING RECONSTRUCTION OF HUMAN SURFACES FROM ORIENTATION DATA

(71) Applicant: Massachusetts Institute of Technology, Cambridge, MA (US)

(72) Inventors: Carlos Sanchez Mendoza, Madrid (ES); Luca Giancardo, Cambridge, MA (US); Tobias Hahn, Cambridge, MA (US); Aurelien Bourquard, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/743,711

(22) PCT Filed: Jul. 15, 2016

(86) PCT No.: PCT/US2016/042513
§ 371 (c)(1),
(2) Date: Jan. 11, 2018

(87) PCT Pub. No.: WO2017/011753
PCT Pub. Date: Jan. 19, 2017

(65) Prior Publication Data
US 2018/0204379 A1   Jul. 19, 2018

Related U.S. Application Data

(60) Provisional application No. 62/192,612, filed on Jul. 15, 2015.

(51) Int. Cl.
*G06T 17/30* (2006.01)
*G06T 17/00* (2006.01)
(Continued)

(52) U.S. Cl.
CPC ............ *G06T 17/30* (2013.01); *A61F 5/02* (2013.01); *G01B 21/20* (2013.01); *G06F 3/011* (2013.01);
(Continued)

(58) Field of Classification Search
None
See application file for complete search history.

(56) References Cited

U.S. PATENT DOCUMENTS 8,686,992 B1   4/2014  Makadia
8,696,458 B2 *  4/2014  Foxlin ............... G07F 17/3209
                                                      345/156
(Continued)

OTHER PUBLICATIONS

International Search Report and Written Opinion for PCT/US16/42513 dated Nov. 29, 2016.
(Continued)

*Primary Examiner* — Jason A Pringle-Parker
(74) *Attorney, Agent, or Firm* — Peter A. Nieves; Sheehan Phinney Bass & Green PA

(57) ABSTRACT

A system constructs a positional contour of a variably contoured surface using data from a 3D capture device. A processor captures data from a tangential orientation capture device and produces a set of relative orientations. The set of relative orientations is transformed with a set of orientation manifold transformer parameters to produce a set of low dimensional orientations. The set of low dimensional orientations and a trained mapping function definition are used to produce a low dimensional point cloud. The low dimensional point cloud is transformed with a set of point cloud manifold transformer parameters, producing a reconstructed synchronized rotationally invariant point cloud.

7 Claims, 13 Drawing Sheets

(51) Int. Cl.
| | |
|---|---|
| A61F 5/02 | (2006.01) |
| G01B 21/20 | (2006.01) |
| G06F 3/01 | (2006.01) |
| G06K 9/00 | (2006.01) |
| G06T 9/00 | (2006.01) |
| G06T 9/20 | (2006.01) |
| G06T 15/04 | (2011.01) |
| A61F 2/50 | (2006.01) |
| G01S 5/16 | (2006.01) |

(52) U.S. Cl.
CPC .......... *G06K 9/00214* (2013.01); *G06T 9/007* (2013.01); *G06T 9/20* (2013.01); *G06T 15/04* (2013.01); *G06T 17/00* (2013.01); *A61F 2/5046* (2013.01); *G01S 5/163* (2013.01); *G06T 2200/08* (2013.01); *G06T 2207/30004* (2013.01)

(56) References Cited

U.S. PATENT DOCUMENTS

| | | | | |
|---|---|---|---|---|
| 9,466,143 | B1* | 10/2016 | Walvoord | G06T 15/00 |
| 9,607,388 | B2* | 3/2017 | Lin | H04N 13/221 |
| 9,691,153 | B1* | 6/2017 | Byrne | G06T 17/20 |
| 9,824,490 | B1* | 11/2017 | Cote | G06T 17/05 |
| 2008/0180448 | A1 | 7/2008 | Anguelov et al. | |
| 2010/0001998 | A1 | 1/2010 | Mandella et al. | |
| 2011/0213259 | A1 | 9/2011 | Voth et al. | |
| 2013/0204411 | A1 | 8/2013 | Clark et al. | |
| 2015/0257682 | A1* | 9/2015 | Hansen | A61B 5/1128 382/103 |
| 2017/0061036 | A1* | 3/2017 | Schmidt | G06F 17/50 |

OTHER PUBLICATIONS

Aris Valtazanos, et al; "Using Wearable Inertial Sensors for Posture and Position Tracking in Unconstrained Environments through Learned Translation Manifolds", 2013 ACM/IEEE International Conference on Information Processing in Sensor Networks (IPSN), Philadelphia, PA, USA, Apr. 2013, pp. 241-252.

Schwartz, et al; "Recognizing multiple human activities and tracking full-body pose in unconstrained environments; Pattern Recognition vol. 45, Issue 1, Jan. 2012, pp. 11-23".

B. Bonnech'ere, V. Sholukha, F. Moiseev, M. Rooze, and S. Van Sint Jan, "From kinect to anatomically-correct motion modelling: Preliminary results for human application," in Games for Health—Proceedings of the 3rd european conference on gaming and playful interaction in health care, 2013, pp. 15-26.

Philip Daubrneier; "Determining Body-Orientation from Sensors in Mobile Devices"; Master's thesis, Technische Universitat Munchen, Jul. 2012.

Thomas Helten, et al: "Real-time Body Tracking with One Depth Camera and Inertial Sensors"; 2013 IEEE International Conference on Computer Vision, Los Alamitos, CA, USA, Dec. 2013, pp. 1105-1112.

Banos, et al; "Kinect=IMU? Learning MIMO Signal Mappings to Automatically Translate Activity Recognition Systems across Sensor Modalities"; IEEE 16th International Symposium on Wearable Computers.

K. Nesenbergs, A. Hermainis, M. Greitans; "A Method for Segment Based Surface Reconstruction from Discrete Inclination Values; Elektronika IR Elektrotechnika, ISSN 1392-1215, vol. 20, No. 2, 2014".

N. Sprynski, et al; "Surface reconstruction via geodesic interpolation"; Computer-Aided Design 40 (2008) 480-492.

Vlasic, et al; "Practical Motion Capture in Everyday Surroundings"; Computer-Aided Design, vol. 40, No. 4, pp. 480—492, Apr. 2008.

O. Sorkine, "Least-squares rigid motion using SVD," ETH Zurich, Tech. Rep., 2009, http://igl.ethz.ch/projects/ARAP/.

L. A. Schwarz, "Machine learning for human motion analysis and gesture recognition," PhD. dissertation, Technische Universitaet Munchen, Jun. 2012.

A. Myronenko and S. Xubo, "Point set registration: Coherent point drift," IEEE Transactions on Pattern Analysis and Machine Intelligence, vol. 12, No. 32, pp. 2262-2275,2010.

D. Schwarz, L. A. ands Mateus and N. Navab, "Discriminative human full-body pose estimation from wearable inertial sensor data," in Lecture Notes in Computer Science, vol. 5903 LNCS, Zermatt, Switzerland, Nov. 2009, pp. 159-172.

M. Scholz, "Nonlinear PCA based on neural networks," Master's thesis, Dep. of Computer Science, Humboldt-University Berlin, Jun. 2002.

Matthias Scholz, "Validation of nonlinear PCA," Neural Processing Letters, vol. 36, No. 1, pp. 21-30, 2012.

\* cited by examiner

SYSTEM AND METHOD FOR PROVIDING RECONSTRUCTION OF HUMAN SURFACES FROM ORIENTATION DATA

CROSS-REFERENCE TO RELATED APPLICATIONS

This application is the National Stage of International Application No. PCT/US16/42513, filed Jul. 15, 2016, which claims the benefit of U.S. Patent Application No. 62/192,612, flied Jul. 15, 2015. The contents of these prior applications are incorporated by reference herein in their entirety.

FIELD OF THE INVENTION

The present invention relates to imaging, and more particularly, is related to providing positional imaging using orientation sensors.

BACKGROUND OF THE INVENTION

During the last decade, the use and development of inertial measurement units (IMUs) has consistently increased in the framework of position estimation, motion capture, human-computer interaction, gaming, wearable sports technology, and medical applications, to name a few. In most cases, the IMU sensors are worn by the subject(s) and can constitute a fully portable system that may potentially integrate into a garment. A single IMU typically combines measurements that are synchronously obtained from gyroscopes, magnetometers, and accelerometers. State-of-the-art IMU sensors are thus able to provide time-resolved data on the three-dimensional (3D) acceleration and orientation corresponding to their own placement. The orientation information obtained from one given IMU at one given time point can be decomposed into a tangential surface vector and a relative rotation angle around this vector, i.e., a quaternion. Even though optical means such as multiple cameras and range cameras are now employed to capture anatomical or other 3D information, IMU sensors are advantageously wearable, small, lightweight, and immune to occlusion problems. IMU sensors thus allow for free user movements outside laboratory or similarly controlled environments. Future technological developments even go towards sensors that are integrated into cloth, making them barely noticeable for their users. This makes the use of IMUs potentially suitable to the assessment of daily activities.

Explicit time-stable positional data can hardly be obtained from IMU sensors alone. Indeed, since positions are obtained by double-integrating accelerations, the corresponding estimation error, for example, originating from electronic noise and sensor limitations, is cumulative. In this context, inertial sensors are thus considered in conjunction with a complementary modality that is not subject to similar drift phenomena. In the context of human-activity assessment, for instance, it has been proposed to complement an initial set of IMU sensors with additional ultrasound sensors to reduce the drift that is commonly observed in purely inertial systems. IMU data has also been combined with monocular-depth-camera measurements to reconstruct full-body poses.

Unfortunately, the combination of IMU sensors with other modalities for joint data acquisition tends to make the overall approach cumbersome and impractical. In particular, such hybrid systems are typically not portable, and thus have limited potential impact in terms of applications although they are more accurate than the sole use of IMU sensors. One solution to this dilemma is to restrict the auxiliary acquisition device to an initial acquisition phase. In that case, instead of aiming at directly inferring and exploiting explicit positional data, the goal is to first learn some underlying (less trivial) relationship between the orientation data obtained from the IMUs and the features of interest to be estimated, using the data initially obtained from the auxiliary acquisition device as reference. This approach has been followed for the estimation of features such as global posture, gesture, and position, as well as for activity recognition, based on skeleton models.

The auxiliary modalities that are used mainly consist in 3D-optical-tracking systems, for example, based on range cameras, that provide explicit "ground-truth-type" measurements of the quantities of interest. During training, both inertial and optical data are to be acquired simultaneously. These data are then analyzed to infer underlying relationships between the inertial-sensor readings and the features extracted as ground truth from the optical measurements. Under suitable conditions, this allows to set the optical system aside in subsequent use, thus benefiting from all aforementioned benefits of IMU-based systems. An advantage of learning-based approaches is the robustness to sensor placement.

A clinically relevant application of wearable-system technology is the measurement and analysis of anatomical surfaces, in particular in the field of orthopedics and in the context of pathologies such as back-surface pain or scoliosis. Now, while the aforementioned works to consider the estimation of body features based on skeleton models, they do not deal with the reconstruction of anatomical surfaces per se. Therefore, there is a need in the industry to address one or more of the abovementioned shortcomings.

SUMMARY OF THE INVENTION

Embodiments of the present invention provide a system for constructing a positional contour of a variably contoured surface. Briefly described, the present invention is directed to a system that constructs a positional contour of a variably contoured surface using data from a 3D capture device. A processor captures data from a tangential orientation capture device and produces a set of relative orientations. The set of relative orientations is transformed with a set of orientation manifold transformer parameters to produce a set of low dimensional orientations. The set of low dimensional orientations and a trained mapping function definition are used to produce a low dimensional point cloud. The low dimensional point cloud is transformed with a set of point cloud manifold transformer parameters, producing a reconstructed synchronized rotationally invariant point cloud.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The components in the drawings are not necessarily to scale, emphasis instead being placed upon clearly illustrating the principles of the present invention. The drawings illustrate embodiments of the invention and, together with the description, serve to explain the principles of the invention.

DETAILED DESCRIPTION

Figure 1:
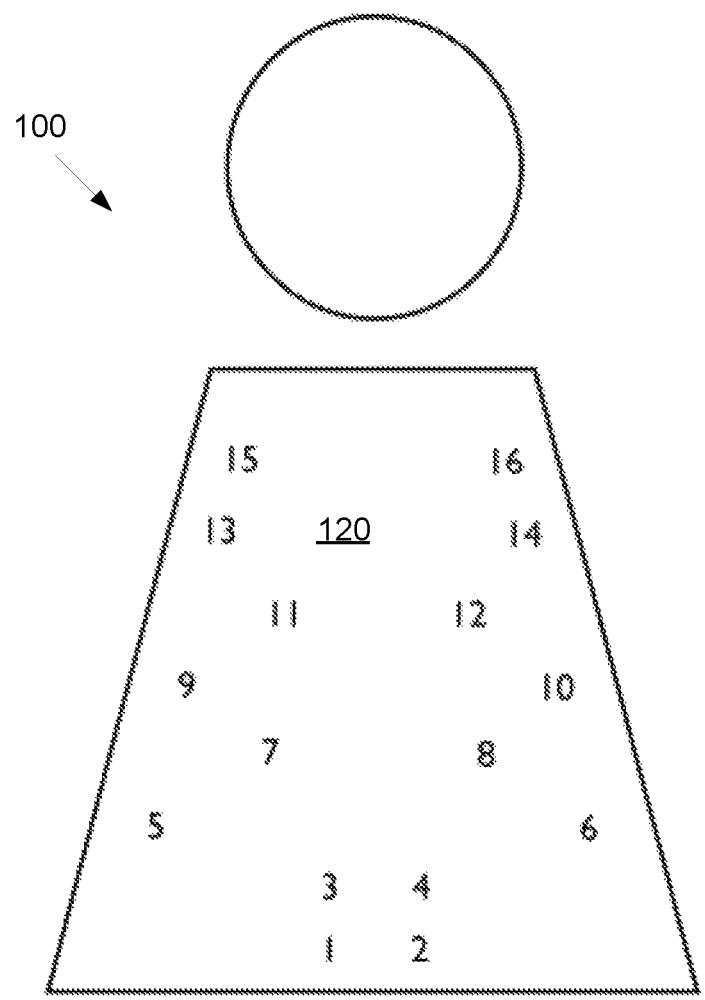
FIG. 1 is a schematic diagram showing exemplary placement of orientation sensors on the back of a person.

The following definitions are useful for interpreting terms applied to features of the embodiments disclosed herein, and are meant only to define elements within the disclosure.

As used within this disclosure, "substantially" means "very nearly," or within typical practical boundaries. For example, "substantially simultaneous" means occurring at the same time allowing for practical time collection differences.

Reference will now be made in detail to embodiments of the present invention, examples of which are illustrated in the accompanying drawings. Wherever possible, the same reference numbers are used in the drawings and the description to refer to the same or like parts.

Exemplary embodiments of the present invention include a system and method that provides a machine-learning-based framework for the estimation of anatomical human body surface point cloud data from IMU data in practical settings. For exemplary purposes, the present description is provided with reference to the human back. It is noted, however, that the present invention is not limited to use on the human back, but may instead be used on different portions of human anatomy. In fact, the present invention need not be limited to use on humans, but may instead be used on animals, or other dynamically moving surfaces.

The placement of the IMU sensors does not require optimization, in the sense that individual sensors need not match specifically predefined locations. This makes the practical use and implementation of the present acquisition system embodiments much more convenient than previous implementations of acquisition systems. In terms of applications, the present exemplary embodiments focus on the assessment of back posture in the context of clinical rehabilitation of idiopathic scoliosis. The implementation of the embodiments may be extended to several other applications, for example, but not limited to sports and gaming, where the analysis of body-surface movements and deformations is relevant.

To streamline implementation, a reconstruction approach may be based on the training of a linear regression model and on the use of particular low-dimensional, affine-invariant representations for both orientation data (as obtained from the IMU sensors) and surface point cloud data, as extracted from the optical acquisitions. These low-dimensional representations are inferred from the training data based on non-linear principal component analysis (PCA) via an auto-encoder neural network, a widely used manifold-learning technique.

Exemplary embodiments of the overall surface-acquisition framework involves the use of motion capture equipment and of IMU sensors. While IMU sensor are worn by the subject during surface acquisition, the optical device, for example, a 3D capture device, may be employed, for example, only during an initial learning stage.

Figure 2:
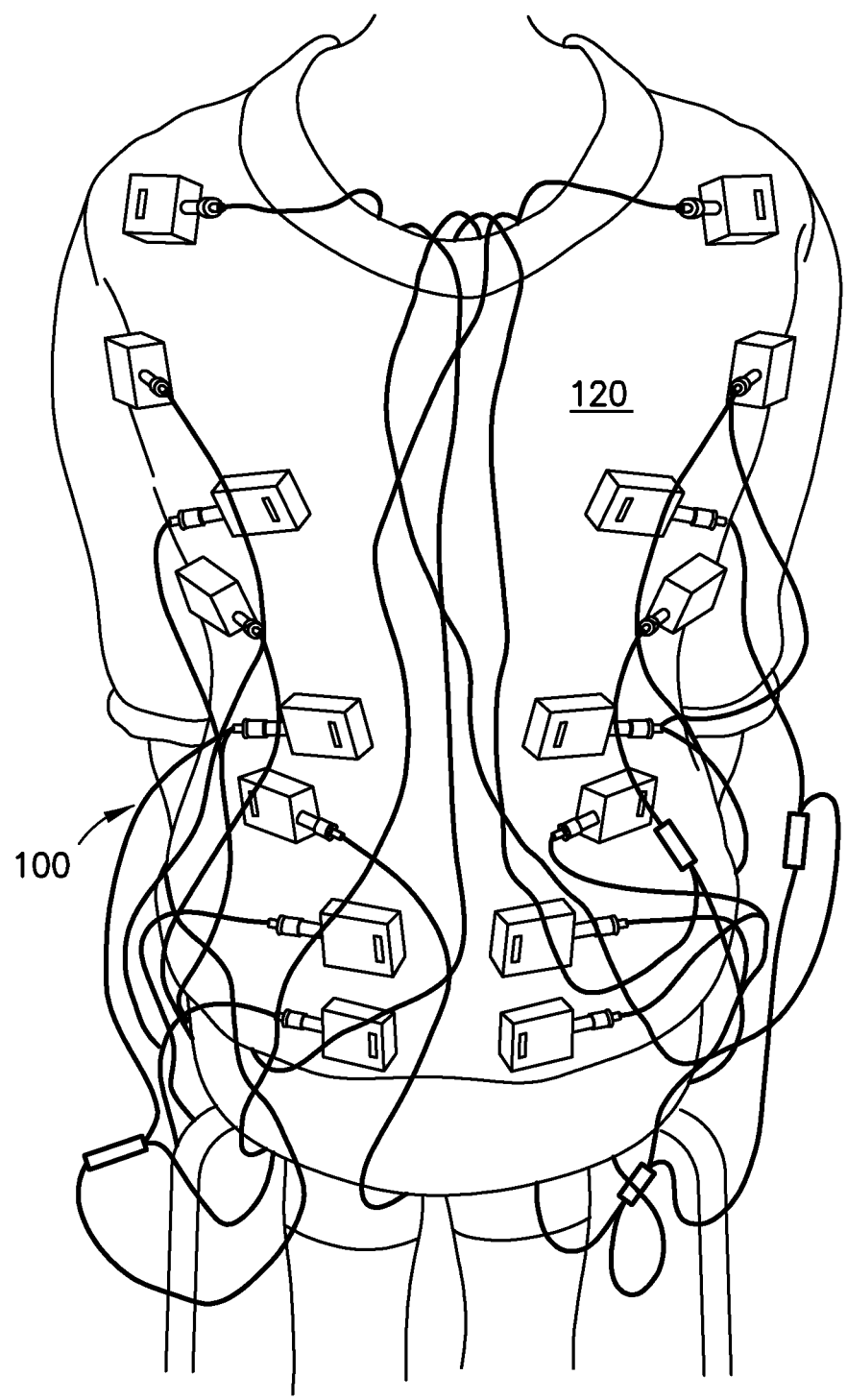
FIG. 2 is a photograph showing exemplary placement of orientation sensors on the back of a person.

The IMU sensors may be embedded in a specifically designed garment and connected to a central hub. The central hub may be a device that collects orientation data from each of the IMU sensors as input and outputs aggregated orientation data. When in active operation mode, this hub regularly communicates the corresponding aggregated orientation data wirelessly to a remote computer station for storage. For example, as shown by FIG. 1, a set of 16 IMU sensors 1-16 may spread throughout the area of the back 120 of a subject 100. The arrangement may also cover the hip and shoulder regions, as shown by FIG. 1. In order to minimize the probability of unwanted displacements during acquisition, the IMU sensors 1-16 may be removably attached on the garment, for example, using strong hook and loop adhesives, or another secure removable adhesive. The garment is preferably tightly fitted to the subject 100. An illustration of the garment prototype worn by a patient as part of a study with subjects is shown in FIG. 2. Each white box corresponds to an IMU sensor 1-16. While FIGS. 1-2 show sixteen IMU sensors 1-16, in alternative embodiments there may be more or fewer IMU sensors 1-16.

Figure 3:
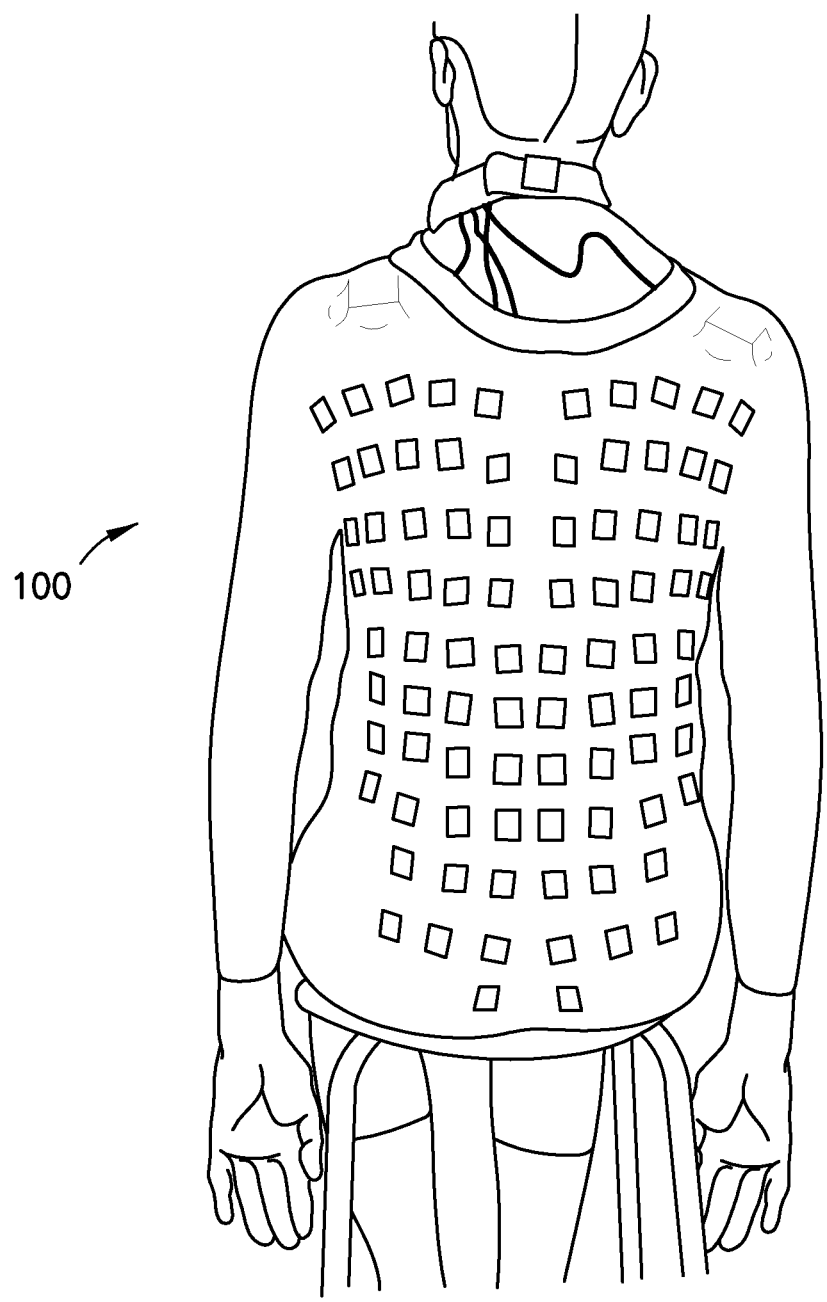
FIG. 3 is a photograph showing exemplary placement of positional sensors on the back of a person.

Once IMU sensors 1-16 are properly placed and attached, the subject 100 puts on one additional garment layer. This new layer contains optical markers that allow for straightforward acquisition of the back surface using motion capture equipment or other optical acquisition equipment and ensure the mechanical stability of the IMUs 1-16. The back surface 120 of the subject is then defined by the 3D coordinates of the markers. The outer garment layer is shown for the same subject in FIG. 3. The white-square optical markers are clearly noticeable in the picture. The central hub (not shown) is installed and fastened in front of the body with a strap placed at the level of the neck.

Figure 4:
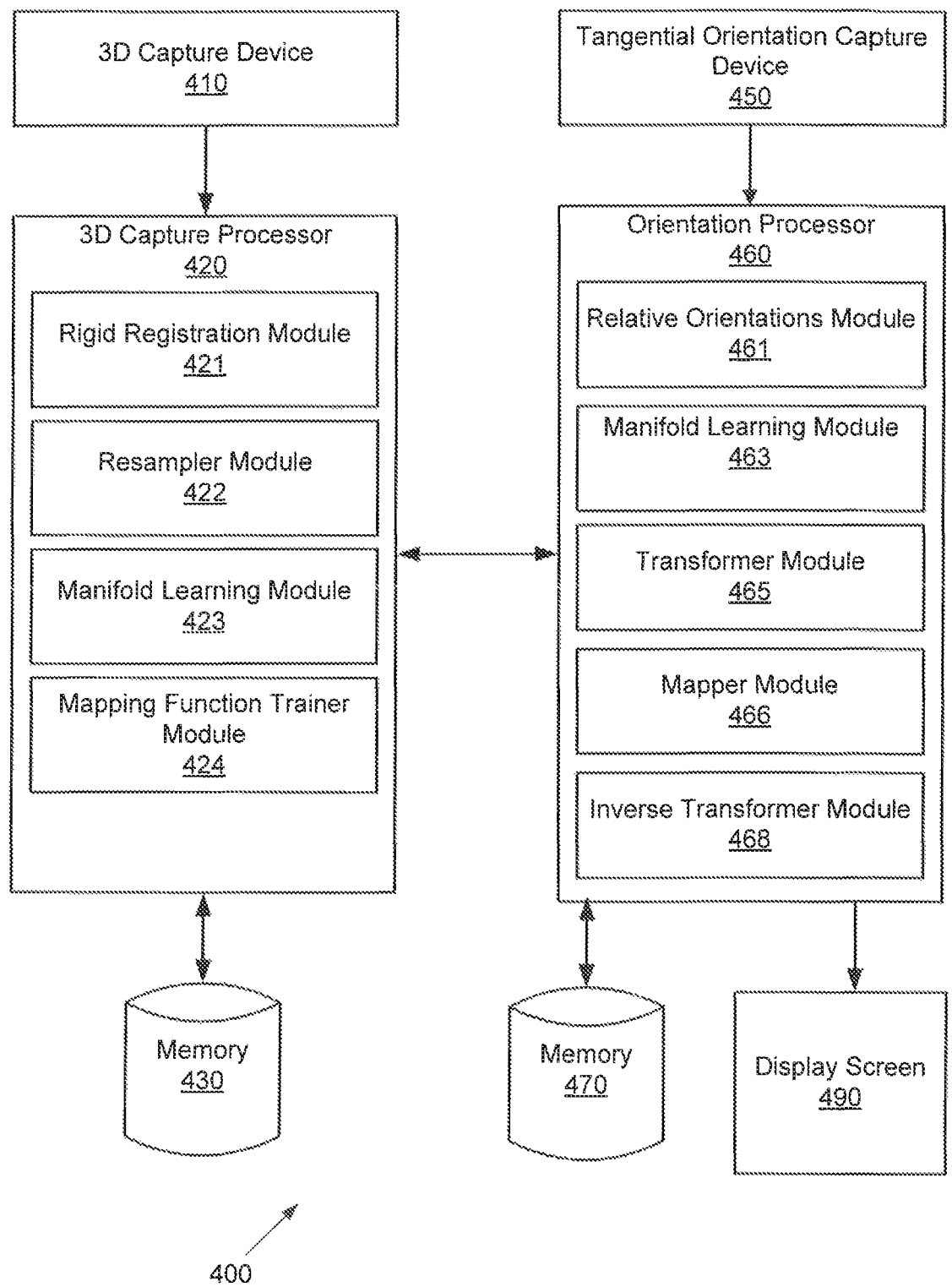
FIG. 4 is a schematic diagram of a system for reconstructing a human back surface from orientation data.

During the initial learning stage, time-resolved subject data are acquired from the motion capture equipment and from the IMU sensors at substantially the same time. Several types of back movements are executed by the subject to guarantee sufficiently complete information. The gathered data are then employed to infer a mapping between the orientation readings provided by the IMU sensors 1-16 and the explicit 3D surface points obtained from the 3D motion capture device 410 (FIG. 4).

During an online phase that follows the learning stage, the mapping that was inferred is exploited to deduce the non-rigid back surface point cloud representation for the subject from IMU data alone. Since the use of the motion capture equipment is not needed, the system becomes fully wearable. It is thus potentially usable outside controlled laboratory or clinical-type environments, provided that the positioning of the IMU sensors relative to the back of the subject remains consistent with the one that was used to infer the mapping. The mathematical notation is provided below.

The input IMU-sensor data corresponding to every acquired sequence consists in a frame-dependent set of local orientations I[f]. Note that the term frame is used here in a distinct context as it refers to a time indexing of sensor readings rather than of optically acquired data as above. The total amount of IMU sensors that are employed is denoted by $N_s$. The set I[f] is defined as $$I[f] = \{O_1[f], \ldots, O_{N_s}[f]\} \quad \text{(Eq. 1)},$$

each element $O_i[f] \in H$ being a quaternion describing the local orientation data provided by the inertial measurement unit sensor i at frame f. Quaternions follow the form a+bi+cj+dk whose associated non-commutative algebra describes general rigid-body orientation in 3D space. Alternative representations of 3D orientation with respect to a global reference frame, such as Euler angles or Direct Cosine Matrices may be easily introduced in the framework. However, the use of quaternions facilitates the best mathematical properties when combining and comparing the orientation readings of several sensors. It should be noted that the time-refresh rate of the IMU sensors and the refresh rate of the motion capture equipment generally do not coincide.

This section describes an exemplary embodiment of a method for reconstructing non-rigid postural surface point cloud data from IMU-sensor data. As mentioned above, the method involves an initial learning stage where the surfaces of interest are acquired with both motion capture equipment and with IMU sensors. This learning stage allows inference of a mapping between IMU readings and the set of surface points in the point cloud to be reconstructed.

An exemplary embodiment of a system 400 for reconstructing a positional contour of a movable surface from orientation sensor data is shown in FIG. 4. A 3D motion capture device 410 includes a plurality of positional sensors disposed upon the surface to be mapped, for example, the back 120 of a subject 100, and is in communication with a 3D capture processor 420 and a memory 430. The 3D capture processor 420 may include functional modules, such as a rigid registration module 421, a resampler module 422, a manifold learning module 423, and a mapping function trainer module 424, among other modules.

A tangential orientation capture device 450 includes a plurality of orientation sensors disposed upon the surface, and is in communication with an orientation processor 460 and a memory 470. The orientation processor 460 may include functional modules, such as a relative orientations module 461, a manifold learning module 463, a transformer module 465, a mapper module 466, and an inverse transformer module 468, among other modules. The functionality performed by the modules 421-424, 461, 463, 465, 466, and 468 is described further below. A video display screen 490 may be used to display a graphical representation of the data output by the orientation processor 450.

While FIG. 4 shows two processors 420, 460 in other embodiments the processing functions and depicted modules 421-424, 461, 463, 465, 466, and 468 may be combined into a single processor or distributed among three or more processors. In particular, the manifold learning module 423, 463 may be implemented as a single shared module. Likewise, the two memories 430, 470 may be combined into a single memory, or may be distributed across three or more memories.

Figure 6:
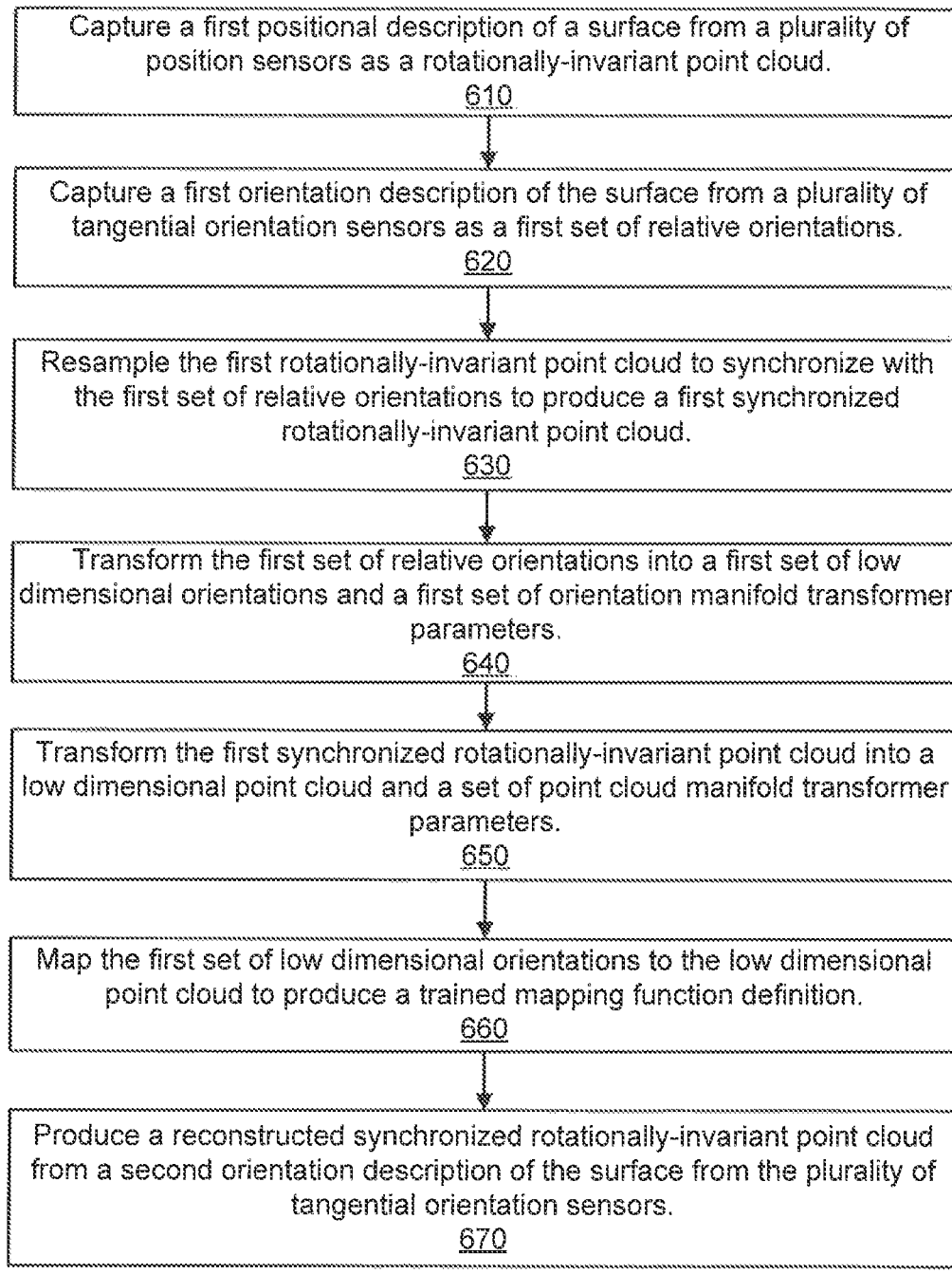
FIG. 6 is a flowchart of an exemplary method for executing the system of FIG. 4.

The memory 430, 470 stores non-transient instructions which are executed by the processor to perform an exemplary method 600 for reconstructing a positional contour of a movable surface, as shown in FIG. 6. It should be noted that any process descriptions or blocks in flowcharts should be understood as representing modules, segments, portions of code, or steps that include one or more instructions for implementing specific logical functions in the process, and alternative implementations are included within the scope of the present invention in which functions may be executed out of order from that shown or discussed, including substantially concurrently or in reverse order, depending on the functionality involved, as would be understood by those reasonably skilled in the art of the present invention. FIG. 6 is a high level description of the method 600, which will be described in further detail thereafter.

As shown by block 610, a first positional description of a surface is collected from the plurality of position sensors, for example, a 3D capture system. The positional description may be captured as a point cloud, $f^g$, which is used to produce a rotationally-invariant point cloud. As shown by block 620, a first orientation description f of the surface is collected from the plurality of tangential orientation sensors. The first orientation description f is a set of absolute orientations, which is processed, for example, by a relative orientations computer, to produce a set of relative orientations.

As shown by block 630, the first rotationally-invariant point cloud is resampled, for example, by a resampling device, to synchronize with the first set of relative orientations, producing a first synchronized rotationally-invariant point cloud. As shown by block 640, the first set of relative orientations is transformed into a first set of low dimensional orientations and a first set of orientation manifold transformer parameters. Likewise, as shown by block 650, the first synchronized rotationally-invariant point cloud is transformed into a low dimensional point cloud and a set of point cloud manifold transformer parameters.

As shown by block 660, the first set of low dimensional orientations is mapped to the low dimensional point cloud to produce a trained mapping function definition. A reconstructed synchronized rotationally-invariant point cloud is produced from a second orientation description of the surface collected from the plurality of tangential orientation sensors, as shown by block 670.

Figure 7:
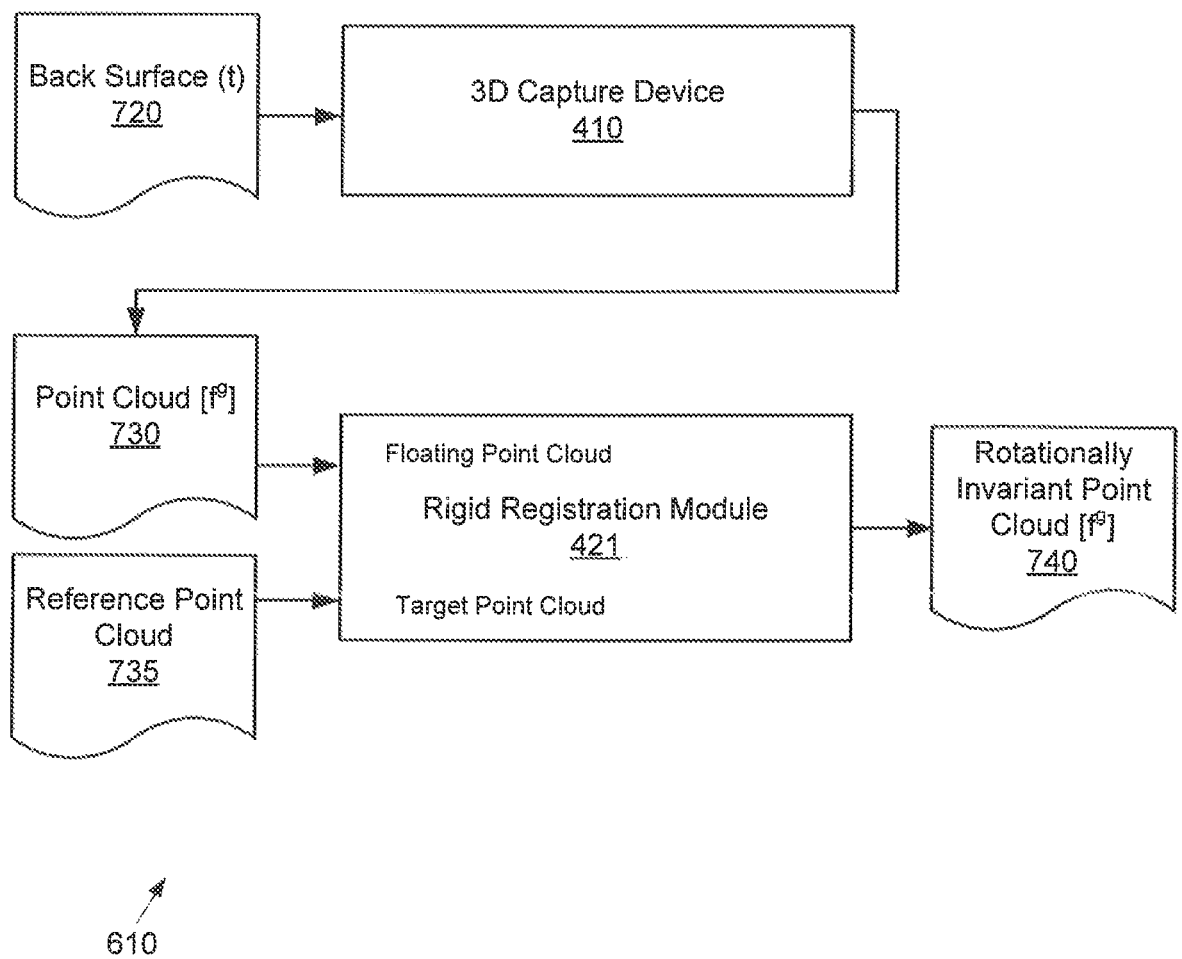
FIG. 7 is a block diagram providing additional details regarding block 610 of FIG. 6.

This system is described in detail as an embodiment for mapping the surface of the back of a human subject. FIG. 7 is a block diagram providing additional details regarding block 610.

A back surface (t) 720 of a subject 100 (FIG. 1) is the source for positional data collected by the 3D capture device 410. For any given continuous time, the back surface 720 geometry may be changing in time as the human subject 100 (FIG. 1) performs postural variations. In one embodiment, this surface is covered with optical reflective markers.

The 3D capture device 410 may be a system capable of acquiring the 3D coordinates of points spread over the captured subject at a certain number of frames per second. In one embodiment, the 3D capture device 410 consists in a set of infrared cameras and optical reflective markers (a.k.a. an optical motion capture system) recording many frames per second (e.g. 100 fps).

The 3D capture device 410 produces a point cloud [fg] 730, including a concatenation of the 3D coordinates of each of the points captured by the 3D capture device 410, at a given frame.

A reference point cloud 735 is a point cloud that is used as reference. In one embodiment, the reference point cloud 735 is chosen as the point cloud [fg] 730 corresponding to a particular frame (i.e. reference point cloud 735=point cloud [fg T]). In another embodiment, the reference point cloud 735 is a proper subset of the points in the point cloud [fg] 730 corresponding to a particular frame (i.e. reference point cloud 735 ⊂ point cloud [fgT]), where T stands for Template.

The rigid registration module 421 transforms the points in the point cloud [fg] 730 using a geometric transform with the purpose of optimizing a metric derived from a comparison between the point cloud [fg] 730 and the reference point cloud 735. In one embodiment, the geometric transform is rigid and allows only for 3D rotations and 3D displacements of the point cloud [fg] 730, and the comparison metric equals to the sum of the distances between each point in the point cloud [fg] 730 and the closest point in the reference point cloud 735.

The rigid registration module 421 produces a rotationally-invariant point cloud [fg] 740. The rotationally-invariant point cloud [fg] 740 is a point cloud that has been geometrically transformed by a rigid registration procedure such that the original global 3D orientation and 3D position of the original point cloud [fg] 730 are modified. For every point cloud [fg] at every frame, a rotationally-invariant point cloud [fg] may be obtained at that frame.

Figure 8:
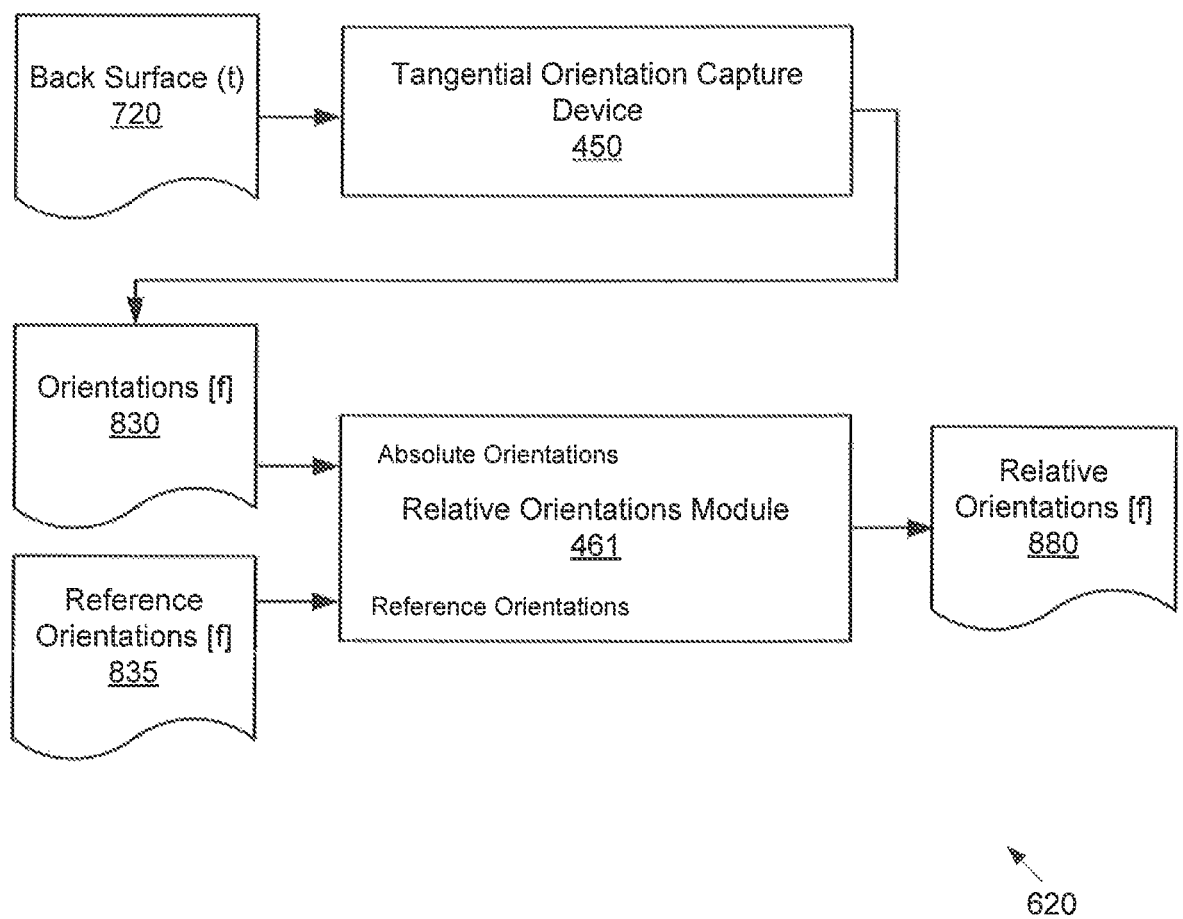
FIG. 8 is a block diagram providing additional details regarding block 620 of FIG. 6.

FIG. 8 is a block diagram providing additional details regarding block 620 of FIG. 6. A first orientation description f of the surface 720 is collected from the plurality of tangential orientation sensors. The first orientation description f 830 is a set of absolute orientations, which is processed, for example, by a relative orientations module 461, to produce a set of relative orientations 880. The tangential orientation capture device 450 may include a plurality of earth-relative orientation sensor units and the infrastructure to acquire the data from each of the units and to process it, either in real time, and/or store them for offline processing and analysis. For example, the Earth-relative orientation sensor units may be commercially available Inertial Measurement Units (IMUs), which include micro-electromechanical gyroscopes, magnetometers and accelerometers, and sensor fusion algorithms which allow the combination of their readings into very accurate and reliable Earth-relative orientations, at a certain number of frames per second.

The tangential orientation capture device 450 produces a set of orientations [f] 830. These orientations include a concatenation of the earth-relative orientations obtained at each of the plurality of earth-relative orientation sensor units in the tangential orientation capture device 450, at a given frame. In one embodiment, the Orientations [f] are a concatenation of the Earth-relative orientations obtained at each of the sensors, and expressed in quaternion form.

A relative orientations module 461 combines a set of reference orientations 835 into a single orientation, and expresses all the orientations [f] (which are absolute orientations) as relative to the computed single orientation. The reference orientations [f] 835 may be, for example, an improper or proper subset of the set of orientations [f] 830 (i.e. reference orientations [f] 835⊆orientations [f] 830). In one embodiment, the reference orientations 835 may be expressed relative to the reference orientations 835 of one particular orientation frame, and averaged to compute a single orientation, and then the absolute orientations 880 are expressed relative to the computed single orientation. The relative orientations module 461 produces a set of relative orientations [f] 880. The relative orientations 880 include a concatenation of the reference-orientations-relative orientations obtained as output of the relative orientations module 461 at a given frame.

Figure 9:
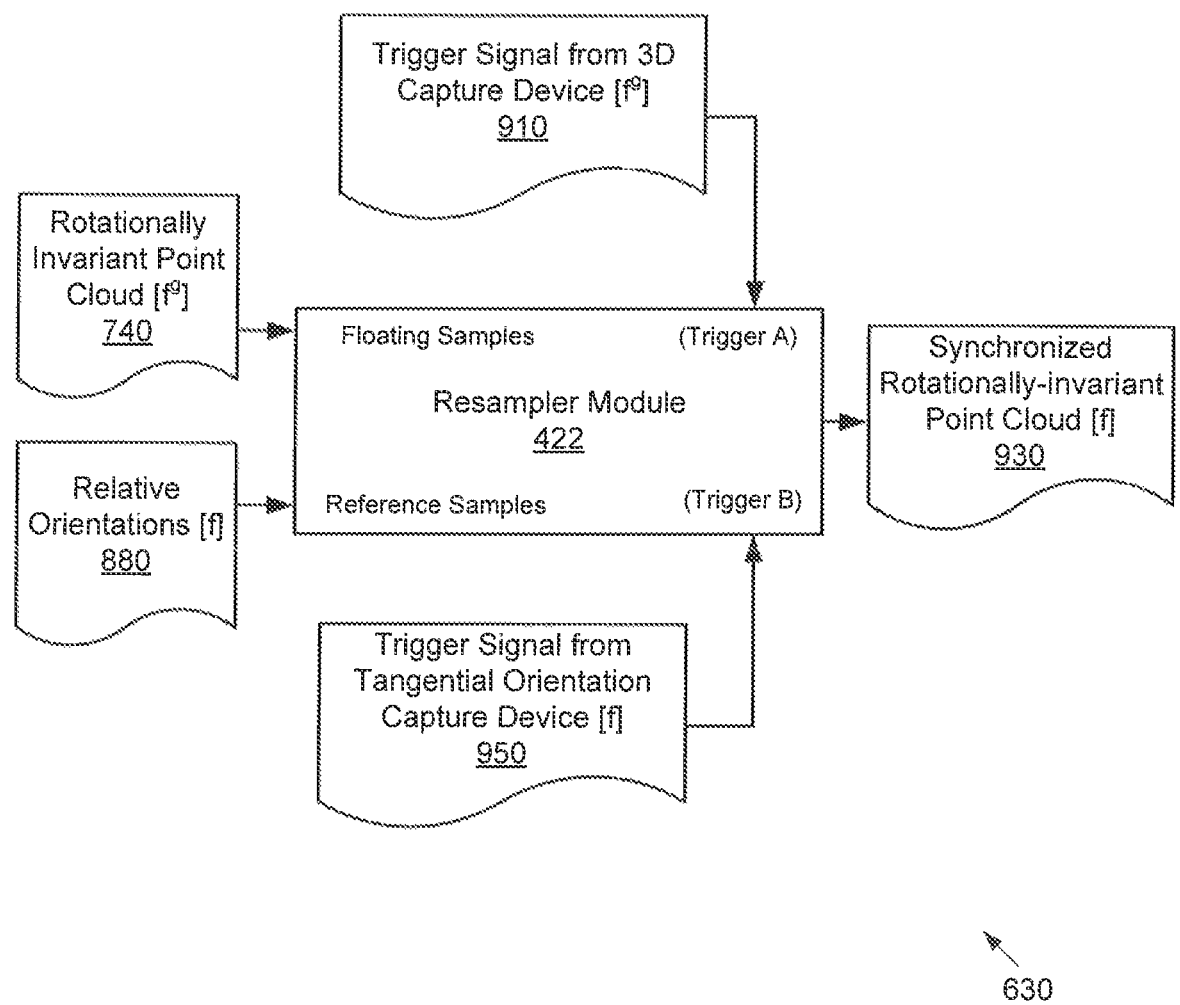
FIG. 9 is a block diagram providing additional details regarding block 630 of FIG. 6.

As shown by FIG. 9, the first rotationally-invariant point cloud 740 is resampled, for example, by a resampling module 422, to synchronize with the first set of relative orientations 880, producing a first synchronized rotationally-invariant point cloud 930.

The resampling module takes as input two different multidimensional sequences defined over distinct discrete time sequences, and resamples the floating samples such that the floating samples take place on the same continuous instants corresponding to the reference samples. In one embodiment, the floating samples are resampled (via interpolation) to optimize a metric comparing the floating samples and the reference samples, where such metric is a correlation between the floating samples and the reference samples. In another embodiment, the floating samples are resampled and interpolated in terms of comparisons between a trigger signal from the 3D capture device 910, and a trigger signal from the tangential orientation capture device 950, as detected in the time scale of both the floating and the reference Samples, and taking into consideration known sampling frequencies of both the 3D capture device 410 and the tangential orientation capture 450. The interpolation technique used by the resampler module 422 may be, for example, a linear interpolation technique, or higher order interpolations such as spline based interpolation.

The resampler module 422 produces a synchronized rotationally-invariant point cloud [f] 930. The synchronized rotationally-invariant point cloud [f] 930 is a synchronized version of the Rotationally-Invariant Point Cloud [fg]740 taking values at any given frame of the relative orientations [f] sequence 880.

Figure 10A:
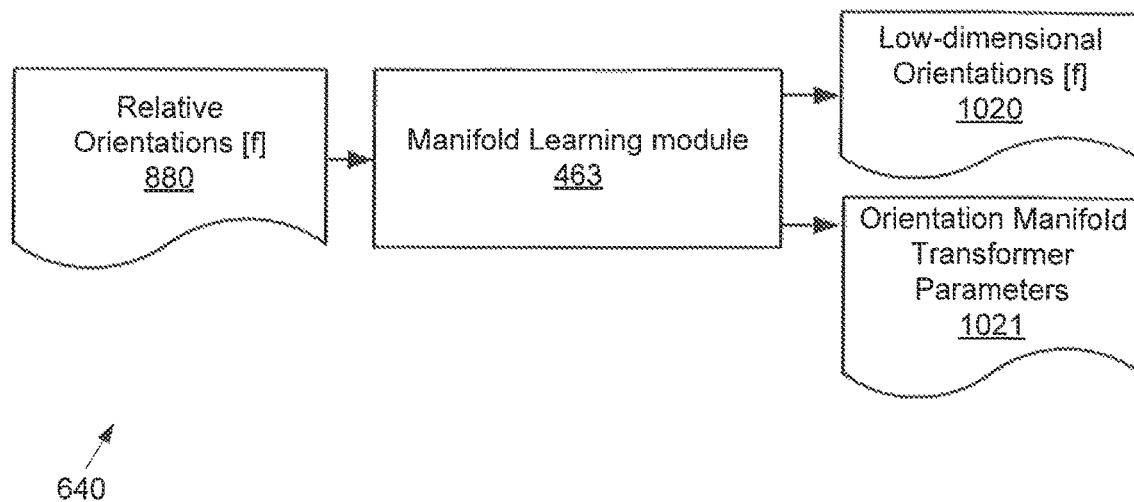
FIG. 10A is a block diagram providing additional details regarding block 640 of FIG. 6.
Figure 10B:
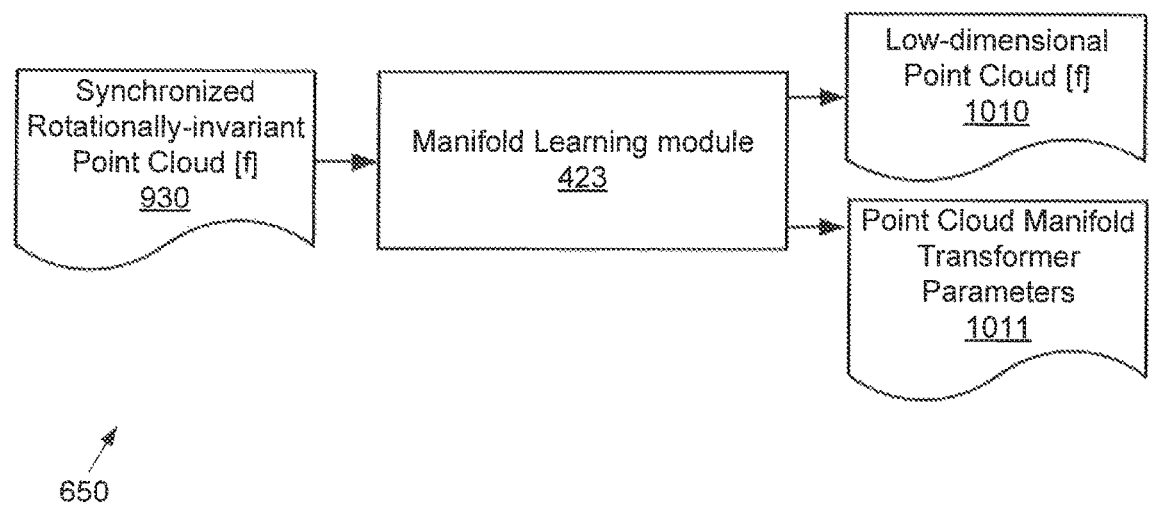
FIG. 10B is a block diagram providing additional details regarding block 650 of FIG. 6.

As shown by FIG. 10A, the first set of relative orientations 880 is transformed into a first set of low dimensional orientations 1020 and a first set of orientation manifold transformer parameters 1021 by a manifold learning module 463. Likewise, as shown by FIG. 10B, the first synchronized rotationally-invariant point cloud 930 is transformed into a low dimensional point cloud 1010 and a set of point cloud manifold transformer parameters 1011 by a manifold learning module 423.

The manifold learning module transforms high-dimensional data representations into low-dimensional data representations by finding the inherent, potentially non-linear structure of the instances in the data over a low-dimensional manifold occurring in the original high dimensional space. In one embodiment, the manifold learning module 423, 463 may incorporate non-linear PCA (an auto encoder neural network). In one embodiment, the low-dimensional representations have seven dimensions 1010, 1020. In other embodiments, the low-dimensional representations may have fewer dimensions, although information may be lost, or more than seven dimensions may be used, although adding dimensions may not significantly improve resolution and may increase noise and computational load.

The low-dimensional orientations [f] 1020 are the result of applying the manifold learning module 463 to the relative orientations [f] 880. Similarly, the low-dimensional point Clouds [f] 1010 result from applying the manifold learning module 423 to the synchronized rotationally-invariant point cloud [f] 930. The orientation manifold transformer parameters produced by the manifold learning module 463 allow for reproduction of the performed manifold learning transformation to new relative orientations [f] 1280 (FIG. 12), described below.

The point cloud manifold transformer parameters 1011 produced by the manifold learning module 423 allow the reproduction of the performed manifold learning transformation to eventual, new synchronized rotationally-invariant point cloud [f] 1250 (FIG. 12), described below.

Figure 11:
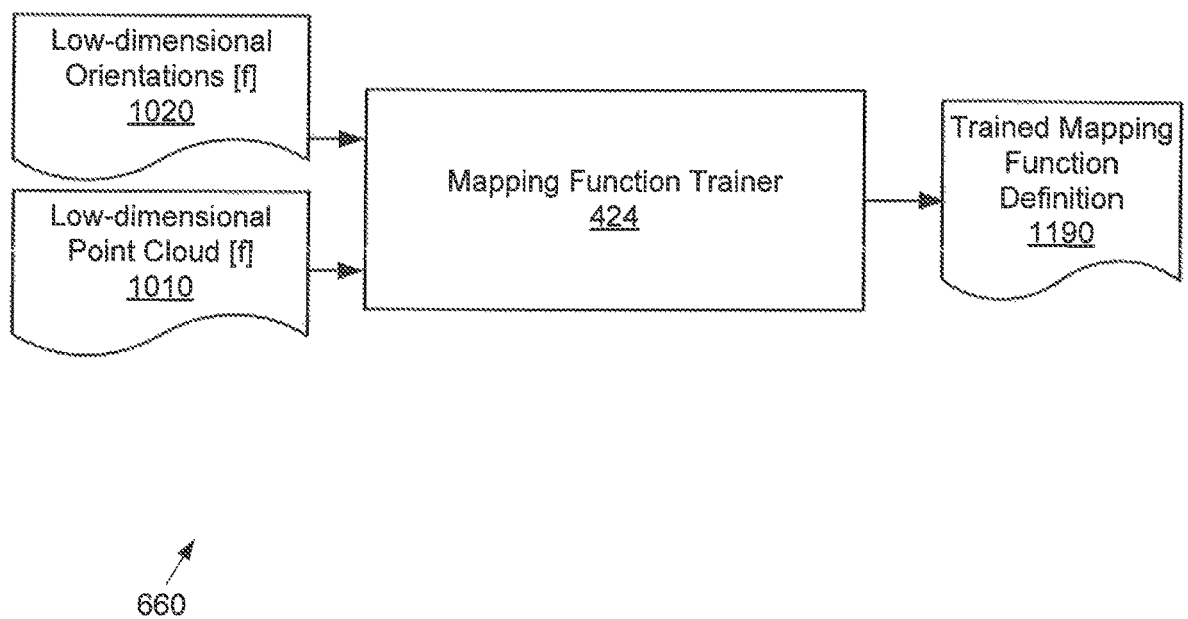
FIG. 11 is a block diagram providing additional details regarding block 660 of FIG. 6.

As shown by FIG. 11, the mapping function trainer 424 maps the first set of low dimensional orientations 1020 to the low dimensional point cloud 1010 to produce a trained mapping function definition 1190. The mapping function trainer 242 computes a function that allows the estimation of low-dimensional Point Clouds 1010 from low-dimensional Orientations 1020 by exploiting a collection of Low-dimensional Orientations [f] and Low-dimensional Point Cloud [f] pairs taking place at matching time frame sets [f] via the optimization of a certain metric relating such input Low-dimensional Point Clouds [f] 1010, and the Low-dimensional Point Clouds [f] resulting from the application of different Mapping Functions to the input Low-dimensional Orientations [f] to produce output Low-dimensional Point Clouds [f]. In one embodiment, the function is assumed to be linear, and the metric to optimize is the sum of the squares of the differences between input Low-dimensional Point Clouds [f] and output Low-dimensional Point Clouds [f], as computed by the function on input Low-dimensional Orientations [f]. The trained mapping function definition 1190 is an optimal mapping function and parameters obtained by the mapping function trainer 424, such that the trained mapping function definition 1190 can be applied to eventual, new low-dimensional orientations [f] 1240 (FIG. 12).

Figure 12:
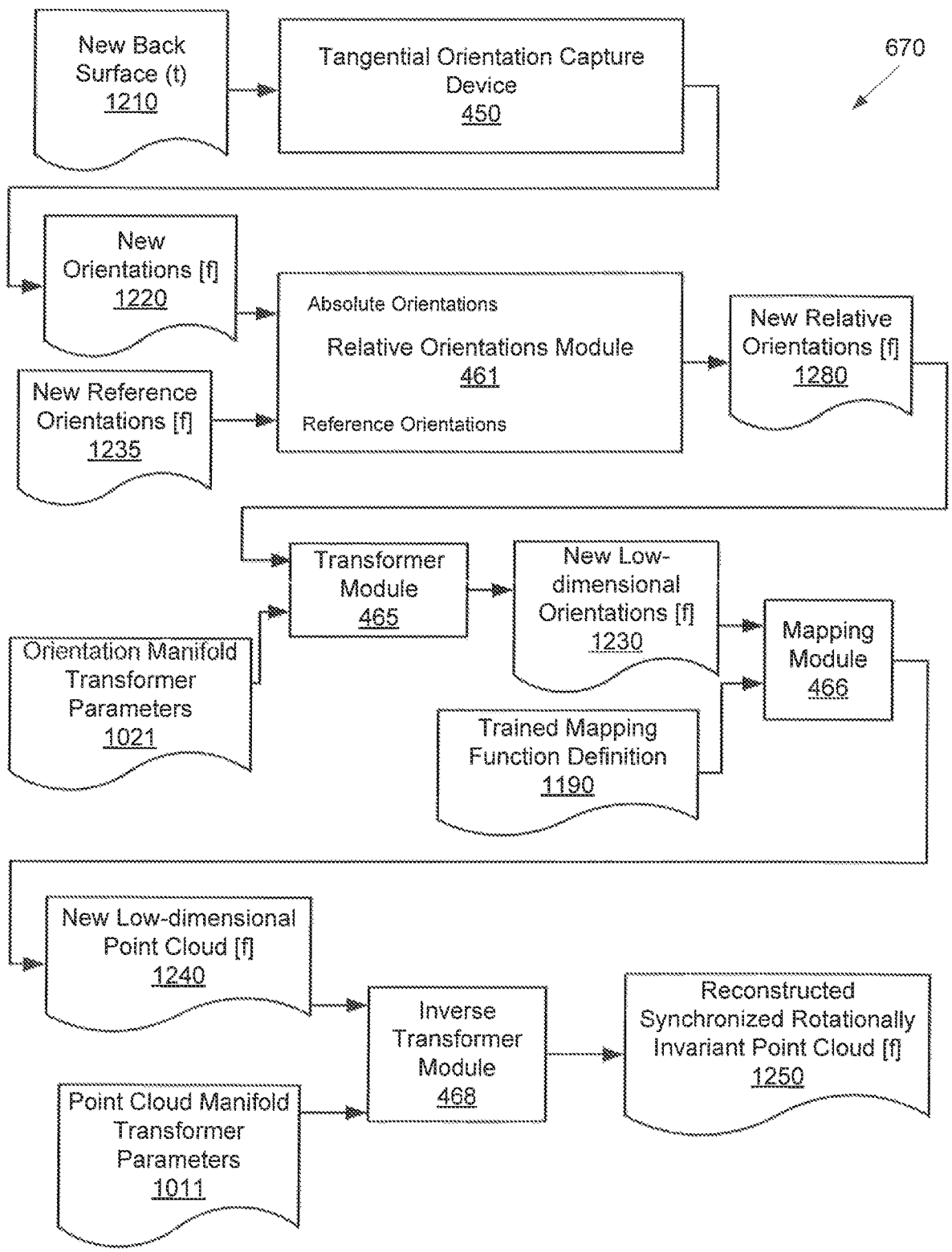
FIG. 12 is a block diagram providing additional details regarding block 670 of FIG. 6.

As shown by FIG. 12, a reconstructed synchronized rotationally-invariant point cloud 1250 is produced from a new orientation description 1220 of the surface collected by the tangential orientation capture device 450. A new back surface (t) 1210 may be, for example, the surface of the back of a subject that differs from the back surface (t) 720 (FIG. 7) based on a change of posture of the subject. For any given continuous time, the surface of a human back geometry may change in time as the human subject performs new postural variations. In one embodiment, this surface is covered with optical reflective markers.

The new back surface (t) 1210 is captured by the tangential orientation capture device 450 to produce new orientations [f] 1220, a concatenation of the new earth-relative orientations obtained at each of the sensors comprised in the tangential orientation capture device 450, at a given frame. In one embodiment, the new orientations [f] 1220 are a concatenation of the Earth-relative orientations obtained at each of the sensors, and expressed in quaternion form. New reference orientations [f] 1235, may include an improper or proper subset of the set of new Orientations [f] 1220 (i.e. New Reference Orientations [f] 1235⊆New Orientations [f] 1220).

As described above regarding FIG. 8, the relative orientations module 461 combines the new reference orientations 1235 into a single orientation, and expresses the absolute new orientations 461 as relative to the computed single orientation, producing new relative orientations [f] 1280 obtained as output of the Relative Orientations Computer at a given frame.

A transformer module 465 transforms the New Relative Orientations [f] 1280 and obtain new low-dimensional orientations [f] 1230 according to the orientation manifold transformer parameters 1021 previously obtained from the manifold learning module 463 (FIG. 10A). A mapping module 466 takes as input the new low-dimensional orientations [f] 1230 and the previously determined trained mapping function definition 1190, and produces a new low-dimensional point cloud [f] 1240 resulting from the applications of the trained mapping function definition 1190 to the input new low-dimensional orientations [f] 1230.

An inverse transformer module 468 inversely transforms the new low-dimensional point cloud [f] 1240 and obtains a reconstructed synchronized rotationally-invariant point cloud [f] 1250 according to the point cloud manifold transformer parameters 1011 previously obtained from the manifold learning module 423 (FIG. 10B).

The reconstructed synchronized rotationally-invariant point cloud [f] 1250 is the main output of the system during normal operation. This output includes concatenated 3D coordinates describing the surface of the back 1220 reconstructed from the readings of tangential orientation capture device 450, without updated readings from the 3D capture device 410 (FIG. 7). Such 3D coordinates are not exactly the 3D coordinates of the surface of the back, but a version that is synchronized to the readings of the tangential orientation capture device 450, and that represents the surface in a positionally and rotationally agnostic manner. The reconstructed synchronized rotationally-invariant point cloud [f] 1250 may be represented, for example, as a graphical representation of the new back surface 1210 on a video display screen 490 (FIG. 4). For example, the orientation processor 460 may include a graphical rendering module (not shown) configured to render the graphical representation of the new back surface 1210 on the video display screen 490 (FIG. 4).

Returning to FIG. 7, the acquired surface point cloud data 730 includes a set of 3D points associated with the centroid of the white-square landmarks placed on the subject garment. The location of these points are determined by the motion capture equipment as a series of back movements are executed. A subsequent rigid-registration operation by the rigid registration module 421 (FIG. 4) produces a rotation-invariant surface representation (rotationally-invariant point cloud [f*] 740). The IMU data that are extracted directly correspond to the orientations I[f] with respect to a global reference frame (i.e. the inertial reference of the Earth). The latter being normalized to ensure rotation invariance as well. As described further below, they are further synchronized in time with the motion capture data so as to obtain a time-consistent learning sequence.

Subsequently, based on the data gathered from the whole learning sequence (FIGS. 7-11), a machine-learning-based approach is used to deduce positional mapping from orientation sensor data. Low-dimensional representations are inferred for both IMU and surface point cloud data based on non-linear PCA implemented via an auto-encoder neural network, providing a mapping structure that is linear and that involves few inter-dependencies. However, other non-linear manifold learning techniques may be employed to obtain equivalent low-dimensional representations. Such trained mappings have suitable generalizing abilities for various settings.

The estimated mappings allow for the reconstruction of the back surface point cloud data of a given subject from IMU sensors alone. Precisely, surface-representing point clouds may be obtained from the corresponding orientation measurements. The overall method 600 involves both training and testing stages is schematized in FIG. 6. The computational details follow.

In order to capture the 3D deformations from tangential orientation data one cannot directly employ the tangential orientations with respect to a global reference frame, as directly provided by the IMUs in I[f]. Instead the relative orientation of each location is obtained on the surface with respect to particular non deforming reference location, or to a body-global orientation.

Two approaches are possible: (1) Choose one of the IMUs as reference orientation and express the orientations of the other IMUs as relative to the chosen orientation, for every frame. This can be achieved with simple quaternion multiplications: multiply the inverse of the reference quaternion to the left of the quaternion for the orientation that is to be expressed relative to the reference orientation. (2) Create a global reference by averaging the quaternions of all IMUs and express the orientations of every IMUs as relative to the obtained reference orientation, for every frame, as in option 1. Notice, that averaging of orientations, represented as quaternions or another form, is non trivial and corresponds to a procedure known as SLERP (spherical linear interpolation). Such SLERP, when working with quaternions can be approximated by direct averaging of the quaternions, as long as the quaternions are sufficiently similar, which can be guaranteed by placing all the sensors with the same initial orientations on the surface of the body for a neutral pose such as the one chosen for template.

Orientation data measured tangential to the surface, and expressed relative to an average orientation (as just explained) is postulated to capture local deformations of the surface, but is completely blind to the global orientation of the surface or its position in 3D space. Accordingly, the exemplary method embodiment estimates a rotationally and translationally invariant point cloud $\mathcal{P}_{ri}[f]$ from $\mathcal{P}_r[f]$ based on a rigid-registration operation, using the 3D coordinates of the points in a template point cloud as a fixed reference to be matched. A template is typically chosen from a point cloud representing the surface in a neutral posture, obtained from one of the first frames of our motion capture point cloud acquisition session.

In each frame, the optimal affine-transformation parameters are determined such that the points in $\mathcal{P}_{ri}[f]$ are closest to the corresponding ones in $\mathcal{P}_t$ in the least-squares sense. The resolution approach is based on singular-value decomposition (SVD), which allows to retrieve the exact transformation parameters non-iteratively to render the original position and orientation equal to that of the fixed template. Thus, using this approach the same point cloud is obtained regardless of its position and orientation with respect to the global reference frame (i.e. the Earth).

To estimate the mapping between the IMU measurements and surfaces extracted as point clouds, I[f] and $\mathcal{P}_{ri}[f]$ is time-synchronized. Both latency and acquisition frequency of the motion capture equipment are distinct from those of IMU sensors in general. External synchronization between the two acquisition modalities can be obtained via hardware (e.g. using a trigger a signal shared between the two acquisition devices, the IMU hub and the motion capture CPU, and adjusting the IMU sampling frequency to that of the motion capture equipment, as the latter is typically slower). However, a signal-based synchronization technique may perform correctly in the absence of trigger signals.

Figure 13A:
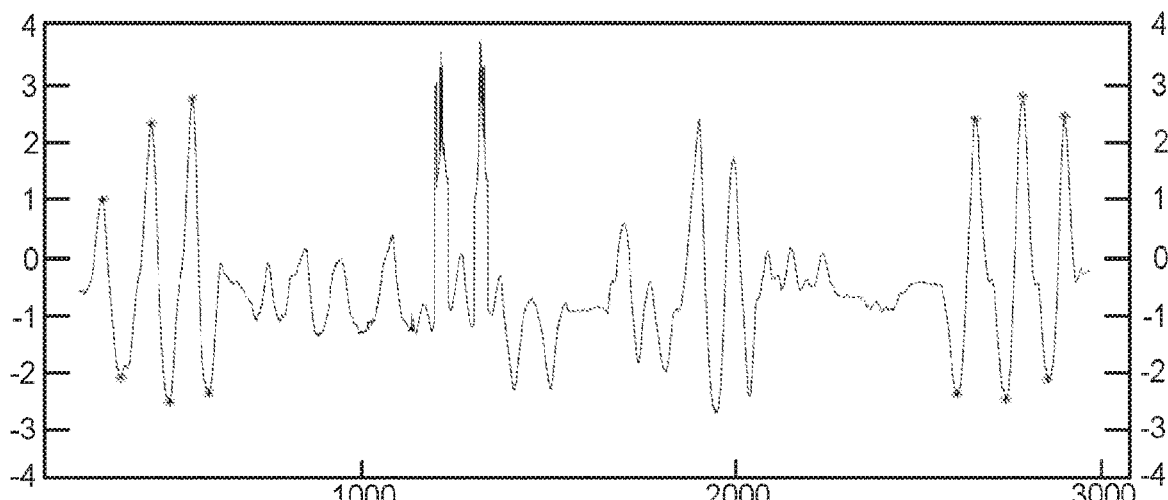
FIG. 13A is a plot showing synchronization of an IMU signal with the corresponding motion capture trajectory signal.
Figure 13B:
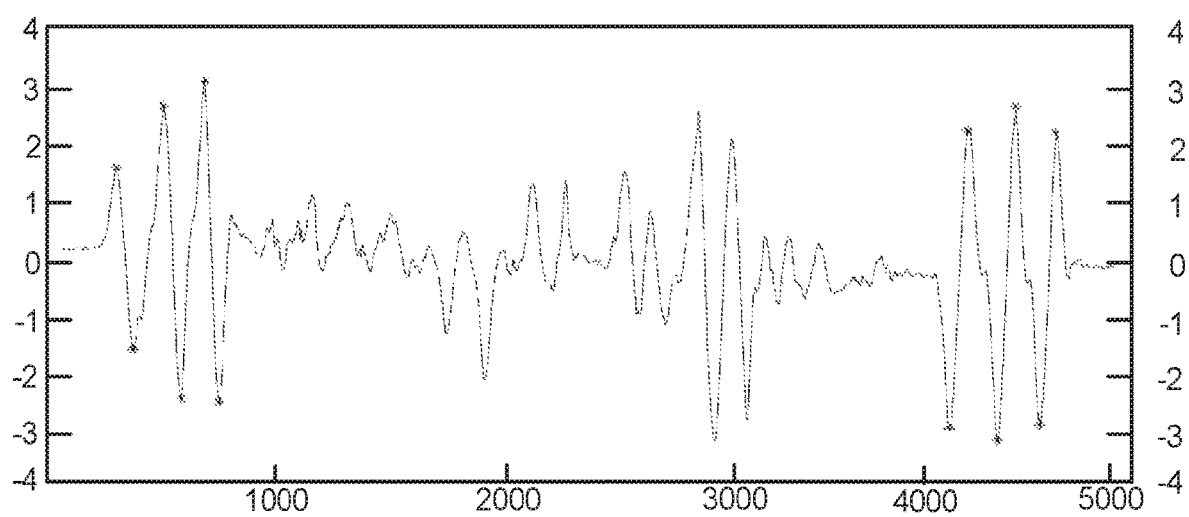
FIG. 13B is a plot of abscissa in FIG. 13A referring to the modality-specific frame index.
Figure 13C:
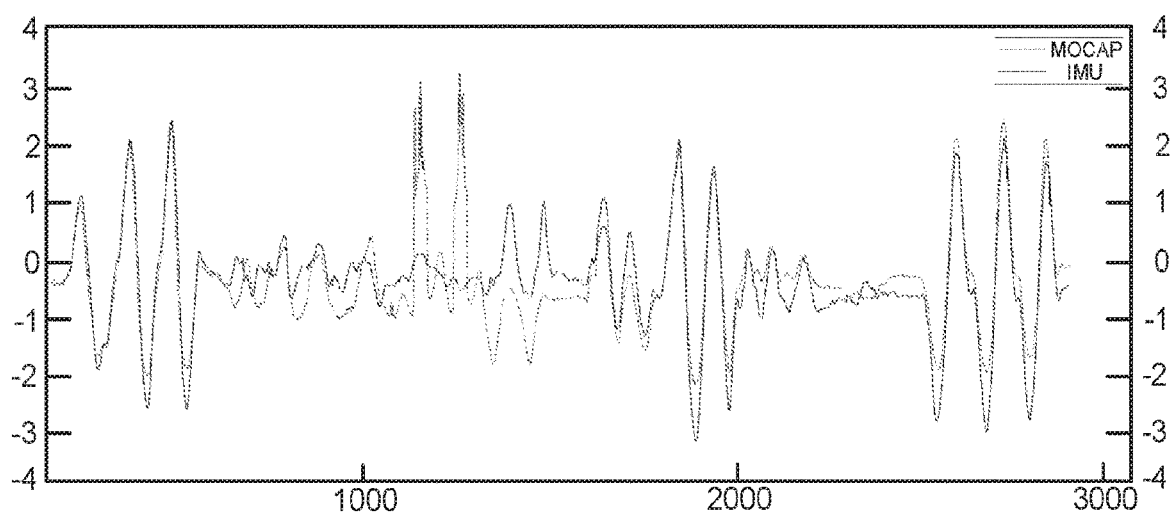
FIG. 13C is a plot superimposing FIG. 13A and FIG. 13B.

Both types of outputs in the learning sequence are matched using a synchronization beacon where the subject executes repetitive movements (e.g. a predefined number of torso rotations), both in the beginning and the end of each recorded sequence. Based on this information, the time evolution of (a) an appropriate Euler angle α[f] may be extracted from the set of absolute measured orientations and (b) a coordinate y[f] may be extracted from the point cloud obtained from the motion capture equipment. Here, the beacon movements are associated with minima and maxima appearing in both real-valued sequences α[f] and y[f], as shown in FIGS. 13A-13C. The corresponding delay and sampling-rate differences are estimated based on linear regression of the respective peak locations. These extracted parameters allow to resample I[f] elementwise for the whole calibration sequence such that the peak locations of the resulting set $I_s[f]$ match those of Note that the time synchronization of both data involves the resampling of the IMU data because its acquisition frequency is typically higher than the one of the motion capture equipment.

FIG. 13A shows synchronization of an IMU signal α[k] (a) with the corresponding motion capture trajectory signal y[k]. The abscissa in FIG. 13B refers to the modality-specific frame index; the variances of both signals are unit-normalized. The result, shown by FIG. 13C, shows y[k] superimposed with the time-resampled version of α[k] that is associated with the estimated corrective delay and sampling rate.

Once the data from the learning sequence are extracted, registered, and synchronized, a function may be estimated that maps every set of $N_s$ IMU measurements $I_s[f]$ to the corresponding set of $N_p$ 3D surface points $\mathcal{P}_{ri}[f]$. The real-valued vectors i[f] and p[f] are constructed containing the lexicographically-ordered components of the corresponding elements $I_s[I]$ and $\mathcal{P}_{ri}[f]$, respectively. Specifically, for every f, $$i=(O_{s1,a},O_{s1,b},O_{s1,c},O_{s1,d},O_{s2,a},O_{s2,b},\ldots),$$

$$p=(P_{ri1,x},P_{ri1,y},P_{ri1,z},P_{ri2,x},P_{ri2,y},\ldots). \quad \text{(Eq. 2)}$$

The mapping between i and p holds at least approximately for every separate frame. This may be expressed as:

$$|h(i[f])-p[f]|<\varepsilon,\forall f, \quad \text{(Eq. 3)}$$

where the vector-valued function h specifies the type of mapping, and where c is a small positive constant associated with the mapping accuracy. The estimate provided by h at every frame f is denoted by $$\tilde{p}[f]=h(i[f]) \quad \text{(Eq. 4)}$$

Note that h is independent off so the estimates rely only on the current-frame measurements. Lower-dimensional representations are proposed below, corresponding to dimensionality-reduction (or down sampling) operators $\mathcal{D}_1$ and $\mathcal{D}_2$, to avoid potential over-fitting, and simplifying the mapping estimation between the measurement and output vectors. Specifically, the mapping estimated between both low-dimensional representations is linear.

According to Eq. (Eq. 2), the vector i[f] includes every separate quaternion coefficient provided by the IMU sensors at given frame f. The components of i[f] are correlated because the non-rigid back surface on which the $N_s$ sensors are placed exhibits a certain degree of spatial regularity. In addition, the quaternion representation of spatial orientation is stable but also subject to regularity due to the constrained range of possible deformations for the human back. A lower-dimensional representation of i[f] is thus derived using non-linear PCA, advantageously identifying non-linear subspace structures, unlike linear PCA.

The specific structure of the low-dimensional measurement representation is adaptive and inferred by applying NLPCA on the set of vectors i[f] which are first normalized with respect to the mean orientations at f to obtain rotation invariance as described in Section 3.1. All frames of the learning sequence are taken into account. According to the low-dimensional manifold subspace that is inferred by the algorithm, low-dimensional vectors of the form i'[f] are found. Formally, $$i'[f] = \mathcal{D}_1\{i[f]\}, \quad (Eq. 5)$$

where $\mathcal{D}_1$ is an operator determined by NLPCA. This operator transforms every given measurement vector into its low-dimensional counterpart with $N_{mc} \ll 4N_s$ components. The mapping h is restricted to only exploit this low-dimensional input information. Accordingly, $$\tilde{p}[f] = h'(i[f]), \quad (Eq. 6)$$

the transform-domain mapping function h' satisfying the property $h(\bullet)h'(D_1\{\bullet\})$.

As specified in Equation (Eq. 2), the vector p[f] concatenates the coordinates of all surface points at frame f. Given its invariance properties, our surface representation reflects the set of possible back-surface deformations for a given subject. In order to capture the relevant modes of deformation and decrease redundancy, we thus propose to employ a low-dimensional representation as in the case of the measurements.

The associated low-dimensional transform $\mathcal{D}_2$ is determined by the same NLPCA algorithm as above, using this time the set of vectors p[f] as input. Accordingly, every surface vector is transformed into a lower-dimensional counterpart of size $N_{sc} \ll 3N_p$ as $$p'[f] = \mathcal{D}_2\{p[f]\}, \quad (Eq. 7)$$

Compared to the original surface, our low-dimensional representation introduces an approximation whose accuracy depends on $N_{sc}$. The surface p[f] is estimated from p'[f] as $$\mathcal{U}_2\{p'[f]\}, \quad (Eq. 8)$$

the operator $\mathcal{U}_2$ being the adjoint of $\mathcal{D}_2$ in some sense. Following the low-dimensional model, the mapping is constrained to be associated with surfaces that are spanned by the low-dimensional coefficients. This yields a final mapping relation $$\tilde{p}'[f] = h''(i'[f]), \quad (Eq. 9)$$

where h'' satisfies the property $$h(\bullet) = U_2\{h''(D_1\{\bullet\})\}. \quad (Eq. 10)$$

According to Equation (Eq. 9), a suitable function h'' must be estimated based on the input and output sets of low-dimensional real-valued vectors i'[f] and p'[f]. In order to minimize the complexity of the model, we constrain our mapping to be of linear form. This reduces our estimation problem to a linear regression and fixes the structure of h'' as $$h''(\bullet) = M\bullet + v, \quad (Eq. 11)$$

where the $N_{sc} \times N_{mc}$ matrix M and the $N_{sc} \times 1$ vector v determine the mapping. The corresponding components are estimated such that they minimize the least-square estimation error.

The estimated mapping allows reconstruction the surface point cloud $\mathcal{P}$ corresponding to any input set of IMU measurements I, provided that the amount $N_s$ of sensors and their placement are consistent with the settings that employed for the learning sequence. Specifically, following vector notation, Eq. 10 and Eq. 11 imply that, given a vector i[f] concatenating the IMU measurements acquired at frame f of a given sequence, $$\tilde{p}[f] = \mathcal{U}_2\{M(\mathcal{D}_1\{i[f]\}) + v\}, \quad (Eq. 12)$$

where the operators, matrix, and vector $\mathcal{D}_1$, $\mathcal{U}_2$, M, and v are structured and specified as described above. The obtained surface point cloud representation is positionally and rotationally agnostic, given that the mapping was trained from positionally and rotationally normalized surface point clouds obtained from the original point clouds obtained from the motion capture equipment.

Figure 5:
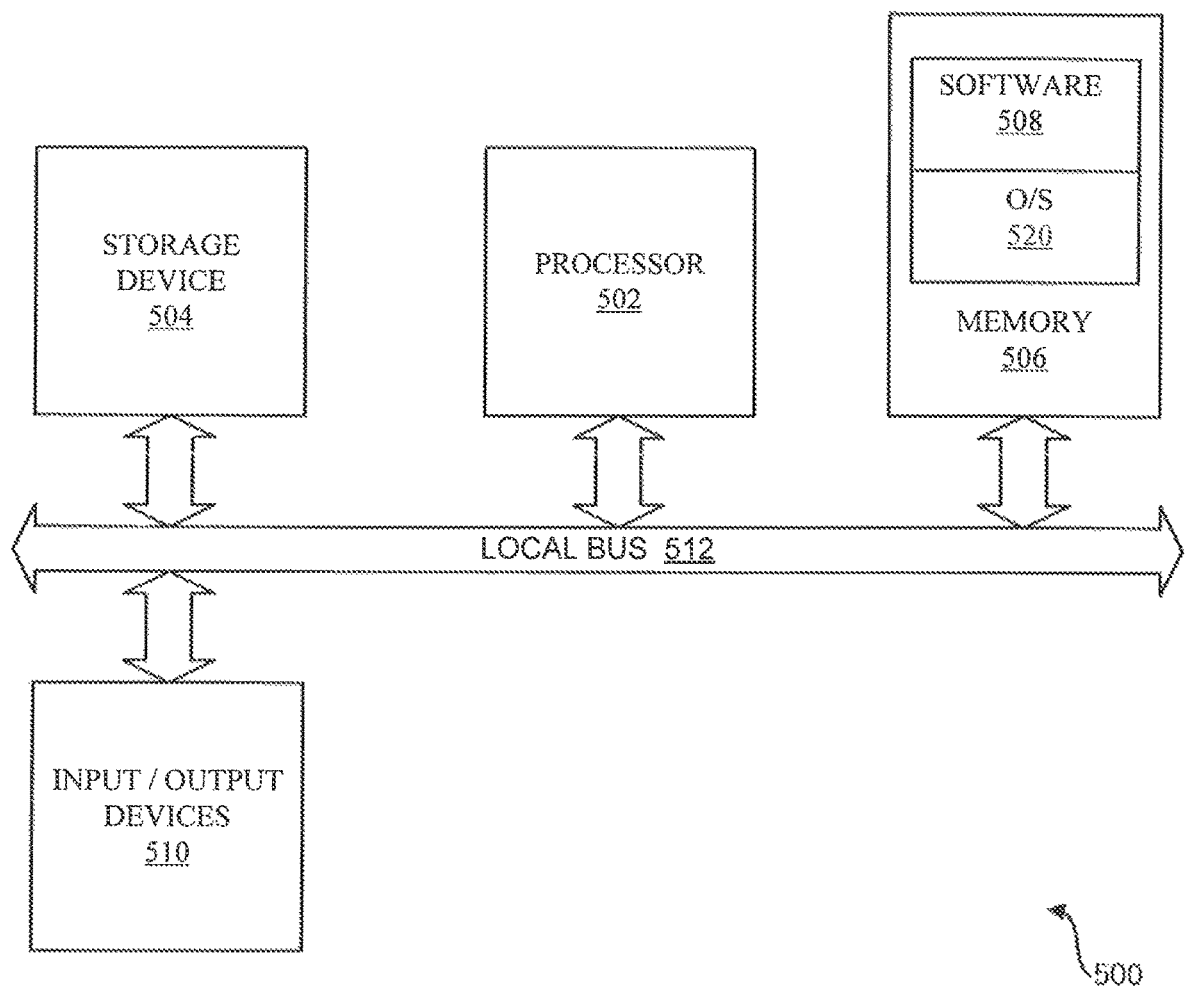
FIG. 5 is a schematic diagram illustrating an example of a system for executing functionality of the present invention.

As previously mentioned, the present system for executing the functionality of the modules 421-424, 461, 463, 465, 466, and 468 described in detail above may be one or more computers, an example of which is shown in the schematic diagram of FIG. 5. The system 500 contains a processor 502, a storage device 504, a memory 506 having software 508 stored therein that defines the abovementioned functionality, input and output (I/O) devices 510 (or peripherals), and a local bus, or local interface 512 allowing for communication within the system 500. The local interface 512 can be, for example but not limited to, one or more buses or other wired or wireless connections, as is known in the art. The local interface 512 may have additional elements, which are omitted for simplicity, such as controllers, buffers (caches), drivers, repeaters, and receivers, to enable communications. Further, the local interface 512 may include address, control, and/or data connections to enable appropriate communications among the aforementioned components.

The processor 502 is a hardware device for executing software, particularly that stored in the memory 506. The processor 502 can be any custom made or commercially available single core or multi-core processor, a central processing unit (CPU), an auxiliary processor among several processors associated with the present system 500, a semiconductor based microprocessor (in the form of a microchip or chip set), a macroprocessor, or generally any device for executing software instructions.

The memory 506 can include any one or combination of volatile memory elements (e.g., random access memory (RAM, such as DRAM, SRAM, SDRAM, etc.)) and non-volatile memory elements (e.g., ROM, hard drive, tape, CDROM, etc.). Moreover, the memory 506 may incorporate electronic, magnetic, optical, and/or other types of storage media. Note that the memory 506 can have a distributed architecture, where various components are situated remotely from one another, but can be accessed by the processor 502.

The software 508 defines functionality performed by the system 500, in accordance with the present invention. The software 508 in the memory 506 may include one or more separate programs, each of which contains an ordered listing of executable instructions for implementing logical functions of the system 500, as described below. The memory 506 may contain an operating system (O/S) 520. The operating system essentially controls the execution of programs within the system 500 and provides scheduling, input-output control, file and data management, memory management, and communication control and related services.

The I/O devices 510 may include input devices, for example but not limited to, a keyboard, mouse, scanner, microphone, etc. Furthermore, the I/O devices 510 may also include output devices, for example but not limited to, a printer, display, etc. Finally, the I/O devices 510 may further include devices that communicate via both inputs and outputs, for instance but not limited to, a modulator/demodulator (modem; for accessing another device, system, or network), a radio frequency (RF) or other transceiver, a telephonic interface, a bridge, a router, or other device.

When the system 500 is in operation, the processor 502 is configured to execute the software 508 stored within the memory 506, to communicate data to and from the memory 506, and to generally control operations of the system 500 pursuant to the software 508, as explained above.

When the functionality of the system 500 is in operation, the processor 502 is configured to execute the software 508 stored within the memory 506, to communicate data to and from the memory 506, and to generally control operations of the system 500 pursuant to the software 508. The operating system 520 is read by the processor 502, perhaps buffered within the processor 502, and then executed.

When the system 500 is implemented in software 508, it should be noted that instructions for implementing the system 500 can be stored on any computer-readable medium for use by or in connection with any computer-related device, system, or method. Such a computer-readable medium may, in some embodiments, correspond to either or both the memory 506 or the storage device 504. In the context of this document, a computer-readable medium is an electronic, magnetic, optical, or other physical device or means that can contain or store a computer program for use by or in connection with a computer-related device, system, or method. Instructions for implementing the system can be embodied in any computer-readable medium for use by or in connection with the processor or other such instruction execution system, apparatus, or device. Although the processor 502 has been mentioned by way of example, such instruction execution system, apparatus, or device may, in some embodiments, be any computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the processor or other such instruction execution system, apparatus, or device.

Such a computer-readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

In an alternative embodiment, where the system 500 is implemented in hardware, the system 500 can be implemented with any or a combination of the following technologies, which are each well known in the art: a discreet logic circuit(s) having logic gates for implementing logic functions upon data signals, an application specific integrated circuit (ASIC) having appropriate combinational logic gates, a programmable gate array(s) (PGA), a field programmable gate array (FPGA), etc.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A system (400) using data at least partially collected and derived from a 3D capture device (410) for constructing a positional contour of a variably contoured surface, comprising:
   a tangential orientation capture device (450); and
   an orientation processor (460) and a memory (470) configured to store non-transient instructions which, when executed by the processor, perform the steps of:
   capturing an absolute orientation description of the surface (1220) collected by the tangential orientation capture device and producing a set of relative orientations (1280);
   transforming the set of relative orientations and a set of orientation manifold transformer parameters (1021) to produce a set of low dimensional orientations (1230);
   mapping the set of low dimensional orientations and a trained mapping function definition to produce a low dimensional point cloud (1240); and
   inverse transforming the low dimensional point cloud with a set of point cloud manifold transformer parameters (1011) and producing a reconstructed synchronized rotationally invariant point cloud (1250).

2. The system of claim 1, further comprising a relative orientations module (461) configured to produce the set of relative orientations.

3. The system of claim 1, further comprising a transformer module (465) configured to produce the set of low dimensional orientations (1230).

4. The system of claim 1, further comprising a mapping module (466) configured to produce the low dimensional point cloud (1240).

5. The system of claim 1, further comprising an inverse transformer module (468) configured to produce the reconstructed synchronized rotationally invariant point cloud (1250).

6. The system of claim 1, further comprising a video display screen (490), wherein the orientation processor is further configured to display a graphical representation of the reconstructed synchronized rotationally invariant point cloud on the video display device.

7. The system of claim 1, wherein the tangential orientation capture device further comprises a plurality of tangential orientation sensors disposed upon the surface.

* * * * *